(12) United States Patent
Nicholson et al.

(10) Patent No.: US 7,354,445 B2
(45) Date of Patent: Apr. 8, 2008

(54) EMBOLIC CONTAINMENT SYSTEM WITH ASYMMETRIC FRICTIONAL CONTROL

(75) Inventors: James W. Nicholson, Dracut, MA (US); Michael S. Noone, Londonderry, NH (US)

(73) Assignee: Medtronic Vascular Inc., Santa Rosa, CA (US)

( * ) Notice: Subject to any disclaimer, the term of this patent is extended or adjusted under 35 U.S.C. 154(b) by 371 days.

(21) Appl. No.: 10/736,411

(22) Filed: Dec. 15, 2003

(65) Prior Publication Data

US 2005/0131450 A1    Jun. 16, 2005

(51) Int. Cl.
*A61M 29/00* (2006.01)
(52) U.S. Cl. ..................................... 606/200
(58) Field of Classification Search ............... 606/200, 606/159; 600/585, 164.13
See application file for complete search history.

(56) References Cited

U.S. PATENT DOCUMENTS

| | | | |
|---|---|---|---|
| 5,497,782 A * | 3/1996 | Fugoso ..................... 600/585 |
| 6,059,814 A | 5/2000 | Ladd |
| 6,270,513 B1 * | 8/2001 | Tsugita et al. ............. 606/203 |
| 6,277,139 B1 | 8/2001 | Levinson et al. |
| 6,544,276 B1 | 4/2003 | Zadno-Azizi et al. |
| 6,620,149 B1 * | 9/2003 | Lenz et al. ................. 604/524 |
| 6,911,036 B2 * | 6/2005 | Douk et al. ................ 606/200 |
| 2004/0236369 A1 * | 11/2004 | Dubrul ...................... 606/200 |

FOREIGN PATENT DOCUMENTS

EP    1 344 502 A    9/2003

OTHER PUBLICATIONS

U.S. Appl. No. 10/099,399, filed Mar. 15, 2002, Douk et al.

* cited by examiner

*Primary Examiner*—Anhtuan T. Nguyen
*Assistant Examiner*—Tuan V. Nguyen
(74) *Attorney, Agent, or Firm*—James F. Crittenden

(57) ABSTRACT

A system for treating a vascular condition, including a hollow guidewire, a core wire inserted through the hollow guidewire, and an embolic containment device. The core wire includes a tapered undulating section carried within the hollow guidewire. The embolic containment device is coupled between a distal end of the hollow guidewire and a distal end of the core wire. The tapered undulating section of the core wire provides frictional control of the embolic containment device based on a direction of core wire translation within the hollow guidewire. A method of treating a vascular condition and a guidewire-based embolic filter system are also disclosed.

19 Claims, 8 Drawing Sheets

805 — Provide Core Wire, Hollow Guidewire and Embolic Containment Device Insert into Vessel of the Body

810 — Axially Translate Core Wire Expand Embolic Containment Device Control Axial Translation

815 — Perform Treatment Capture or Contain Embolic Material

820 — Axially Translate Core Wire in Other Direction Contract Embolic Containment Device Control Axial Translation

825 — Remove Core Wire, Hollow Guidewire and Embolic Containment Device

EMBOLIC CONTAINMENT SYSTEM WITH ASYMMETRIC FRICTIONAL CONTROL

FIELD OF THE INVENTION

This invention relates generally to catheters and guidewire deployment of catheter-based treatment tools. More specifically, the invention relates to a guidewire-based embolic containment system with tailored, asymmetric frictional control.

BACKGROUND OF THE INVENTION

Minimally invasive intravascular procedures such as balloon angioplasty and stent placement are important vascular disease treatments for opening vessel blockages of atherosclerotic plaque and thrombi, thereby improving blood flow. A variety of methodologies have been developed for treating vascular blockages, which may involve mechanically removing or reducing the size of the occlusions during thrombectomy, atherectomy, balloon angioplasty, or stenting procedures.

Distal embolization of particulate matter can complicate treatment when embolic particles dislodge while occlusive material is being dilated or cut, and then move downstream from the constricted area to incur a blockage elsewhere and potentially trigger a myocardial infarction, ischema or other complication.

Various interventional systems and methods have been proposed and developed to prevent dislodged embolic material from entering the blood stream and to facilitate the removal of emboli from the blood, thereby reducing the possibility of complications. Medical practitioners have used occlusion devices, filters, lysing and aspiration techniques for removing embolic material. Treatment procedures employing occlusion balloon catheters and aspiration catheters have been developed to help prevent potentially embolic debris from migrating with the blood stream. The occlusion balloon catheter blocks or impedes blood flow while the aspiration catheter aspirates and removes embolic material from the area of the stenosis. Another common embolic containment procedure uses a wire-deployed emboli filter to trap emboli generated during treatment while permitting blood to flow through the filter.

Expandable embolic filters, which are conventionally fixed to the distal end of a guiding wire, have various configurations such as a mesh basket, a tube with multiple laser-drilled holes, a conical basket, a radially expandable mesh, or a structure with a distal coil wound about struts that form a hinge-type connection. Some filters are opened and closed in an umbrella-like fashion so that in the open position, the filter substantially fills the cross-section of the body lumen, whereas in the closed position, the filter with captured emboli is reduced in size to pass through the vessel lumen for removal.

Emboli filters as well as various other intravascular devices may be moved, opened, closed, or otherwise deployed with a wire. For example, a core wire moves slidable push-pull rods that open and close an embolic filter, as described in "Filter for Filtering Fluid in a Bodily Passageway," Ladd, U.S. Pat. No. 6,059,814 issued May 9, 2000. The filter is expanded or contracted by pushing or pulling the core wire relative to the shaft of the hollow guidewire, thus controlling the relative axial positions of the filter ends.

Details of a filter or an occluder for capturing particulate in the vessels of a patient are found in Douk, et al., "Guidewire Apparatus for Temporary Distal Embolic Protection," pending U.S. patent application Ser. No.10/099,399 filed Mar. 15, 2002, the contents of which are hereby incorporated by reference in their entirety.

One use of a friction-inducing wavy core wire in a valve mechanism for a balloon occlusion catheter is described in "Exchange Method for Emboli Containment," Zadno-Azizi et al., U.S. Pat. No. 6,544,276 issued Apr. 8, 2003, the contents of which are hereby incorporated by reference in their entirety. The catheter includes a low-profile catheter valve with a movable sealer portion positioned within the inflation lumen of a catheter. The sealer portion forms a fluid tight seal with the inflation lumen by firmly contacting the entire circumference of a section of the inflation lumen. The sealer portion is positioned proximate to a side-access inflation port on the catheter, establishing an unrestricted fluid pathway between the inflation port and an inflatable balloon on the distal end of the catheter. The sealer portion can be moved to a position distal of the inflation port, thereby preventing fluid from being introduced into or withdrawn from the balloon via the inflation port. The wavy core wire induces a desired level of relatively constant friction to prevent the valve from inadvertently opening or closing.

With the aforementioned filter system and other medical catheter systems having core wires, it is important to control the movement of the devices that are moved, pushed and pulled axially by the core wire within a hollow guidewire or catheter. An improvement to such wire-controlled devices of catheter systems would provide greater control in the moving, positioning and locking of the devices. Preferably, differences in the frictional forces between the pushing and pulling of the wire could be distinguished by a medical practitioner, thereby increasing the performance of the medical devices used during the treatment of vascular conditions.

SUMMARY OF THE INVENTION

One aspect of the invention provides a system for treating a vascular condition, including a hollow guidewire, a core wire inserted through the hollow guidewire, and an embolic containment device coupled between a distal end of the hollow guidewire and a distal end of the core wire. The core wire includes a tapered undulating section that provides frictional control of the embolic containment device based on a direction of axial translation within the hollow guidewire.

Another aspect of the invention provides a method of treating a vascular condition that employs a core wire inserted through a hollow guidewire and an embolic containment device coupled between a distal end of the hollow guidewire and a distal end of the core wire. The core wire includes a tapered undulating section carried within the hollow guidewire. The core wire axially translates in a first direction relative to the hollow guidewire and the embolic containment device expands. The axial translation is controlled in the first direction based on frictional resistance between the tapered undulating section and an internal surface of the hollow guidewire.

Another aspect of the invention is a guidewire-based embolic filter system including a hollow guidewire and a core wire inserted through the hollow guidewire. The core wire includes frictional control means for providing control of the expansion and contraction of an embolic filter based on a translational direction of the core wire within the hollow guidewire.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings. The drawings are illustrative and not to scale.

BRIEF DESCRIPTION OF THE DRAWINGS

Various embodiments of the present invention are illustrated by the accompanying figures, wherein:

FIG. 8 shows a flow diagram of a method of treating a vascular condition, in accordance with one embodiment of the current invention.

DETAILED DESCRIPTION OF THE PRESENTLY PREFERRED EMBODIMENTS

Figure 1:
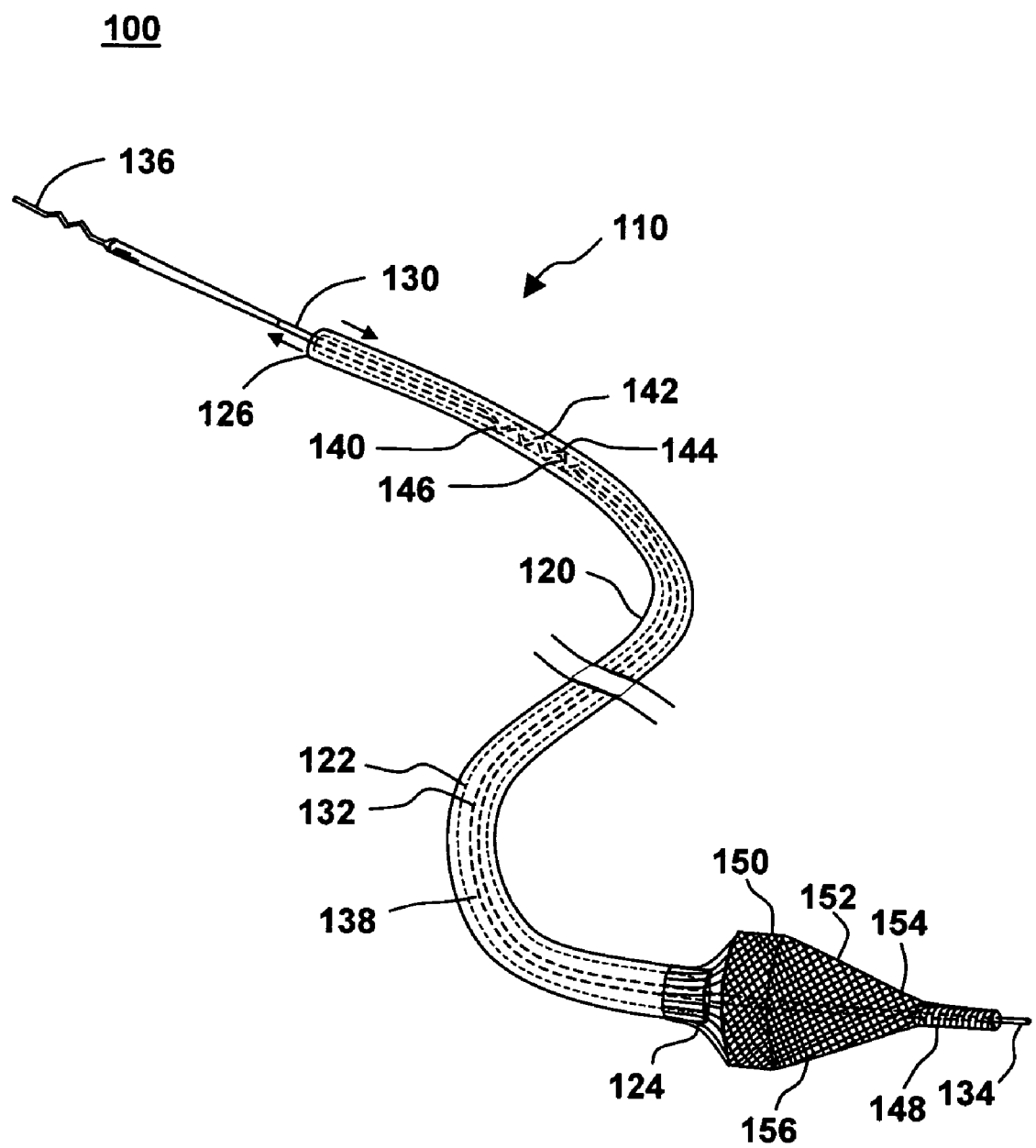
FIG. 1 illustrates a system for treating a vascular condition, in accordance with one embodiment of the current invention.

FIG. 1 illustrates a system for treating a vascular condition, in accordance with one embodiment of the present invention at 100. Embolic containment catheter 110 of vascular condition treatment system 100 includes hollow guidewire 120, core wire 130 having tapered undulating section 140 carried within hollow guidewire 120, and embolic containment device 150. Embolic containment device 150 is coupled between distal end 124 of hollow guidewire 120 and distal end 134 of core wire 130. Core wire 130 is pushed or pulled relative to hollow guidewire 120 to operate embolic containment device 150. Tapered undulating section 140 provides frictional control of embolic containment device 150 based on the direction of axial translation of core wire 130 within hollow guidewire 120. The friction helps control embolic containment device 150 during expansion and contraction, as well as retain and hold embolic containment device 150 in either an expanded or contracted configuration.

Embolic containment device 150 may be actuated after distal end 124 of hollow guidewire 120 is inserted through an incision in the body, directed through a vascular path and positioned at the desired location. Embolic containment device 150 comprises, for example, an embolic filter or an occluder. When actuated into an expanded configuration, embolic filter 152 captures and contains embolic material within a net or basket for extraction when the filter is removed from the body. When actuated into an expanded configuration, an occluder, described more fully with respect to FIG. 3, blocks fluid flow through arteries or veins and contains embolic material within a confined, stagnant portion of the vessel. The embolic material is removed, for example, by aspiration, prior to contracting and removing the occluder.

Vascular treatment system 100 has a low cross-sectional profile, similar to a conventional guidewire, so that entry into the body and positioning of embolic containment device 150 distal to the treatment site within the vessel has minimal impact on the vessel walls. After embolic containment device 150 is positioned distal to the treatment site, the small cross-sectional area of hollow guidewire 120 allows other catheter-based tools such as stent-delivery catheters, dilation catheters, or angioplasty balloon catheters to be placed over hollow guidewire 120 and advanced to the treatment site.

Vascular treatment system 100 may be used with other treatment catheters, such as stent-delivery catheters, aspiration catheters, inspection catheters, measurement catheters, angioplasty catheters, atherectomy catheters, drug-delivery catheters, ultrasound devices, measurement devices, laser catheters, imaging catheters, treatment catheters or therapy catheters. Treatment of vascular conditions may include the prevention or correction of various ailments and deficiencies associated with the cardiovascular system, the cerebrovascular system, urogenital systems, biliary conduits, abdominal passageways and other biological vessels within the body. For example, vascular treatment system 100 can be used in conjunction with a dilation catheter, which enlarges occluded blood vessels by inflating a balloon that is attached near the distal end of the dilation catheter.

Embolic containment catheter 110 is inserted into the vasculature through, for example, a small puncture site at the femoral artery and advanced to the treatment site. After it has been positioned, embolic containment device 150 is expanded and temporarily anchored to the vascular wall to filter or block the flow of blood through the vessel. The long, flexible, small-diameter hollow guidewire 120 may then be used to guide other treatment catheters over hollow guidewire 120. Over-the-wire and rapid-exchange types of catheters may be used in conjunction with hollow guidewire 120.

Embolic containment device 150 is advanced through vessels in the body, guided in part by steerable distal end 134 of core wire 130. Once positioned, embolic containment device 150 may be expanded to an open position by movement of core wire 130 within hollow guidewire or by movement of hollow guidewire 120 over a relatively stationary core wire 130. In one example, pushing the hollow guidewire 120 further into the body while retaining core wire 130 in a stationary position expands and enlarges embolic containment device 150. In another example, pulling core wire 130 while retaining hollow guidewire 120 in a relatively stationary position expands and enlarges embolic containment device 150. In other embodiments, embolic containment device 150 expands as either hollow guidewire 120 is pulled or core wire 130 is pushed. Opposite motions in each of these examples will close, compress, collapse or otherwise contract embolic containment device 150 prior to extraction from the body.

Made from extruded or welded materials such as stainless steel or nitinol, hollow guidewire 120 is an elongate, tubular member with thin walls and a small diameter that flexibly adapts to sinuous paths of the vasculature. In one example, hollow guidewire 120 has an outer diameter of 0.014 inches and an inner diameter on the order of 0.009 inches, with a length between 135 centimeters and 300 centimeters. The length of hollow guidewire 120 may be on the order of 300 centimeters, allowing over-the-wire (OTW) catheters to be inserted into the body once hollow guidewire 120 is in place. In another example, hollow guidewire 120 may be on the order of 175 centimeters in length, suitable for guiding treatment catheters of the rapid-exchange, telescope, multi-exchange and/or zipper types. A sleeve or liner (not shown) may be positioned within hollow guidewire 120 to center core wire 130 disposed therewithin and to reduce sliding friction between hollow guidewire 120 and core wire 130.

Core wire 130, formed from a wire of stainless steel, nitinol or other suitably flexible and strong material, extends through hollow guidewire 120 and is slidably disposed therein. Distal end 134 of core wire 130 may be selectively flattened or ground to aid in steerability. A coiled spring 148 or other flexible member may be attached to or near distal end 134 of core wire 130 to provide a desired amount of flexibility or rigidity as core wire 130 is advanced through the body. Embolic containment device 150 may be attached with an epoxy, solder or other suitable material to a proximal end of coiled spring 148 or to the body of core wire 130 near distal end 124 of hollow guidewire 120. Proximal end 136 of core wire 130 may be selectively flattened, crimped or ground to aid in the connection of handles that help control the movement of core wire 130 within hollow guidewire 120. These alterations may also allow an extension wire to temporarily lock onto proximal end 136 of core wire 130, effectively increasing the working length of core wire 130. Hollow guidewire 120 may have radiopaque markers and other indicia that help a medical practitioner determine the location of embolic containment device 150. Mechanical stops may be added onto hollow guidewire 120 to provide greater kinesthetic feedback on the deployment state of embolic containment device 150.

A coating 138 may be disposed on at least a portion of core wire 130. Coating 138 reduces friction between coated portions of core wire 130 and inner surface 122 of hollow guidewire 120. For example, coating 138 covers portions of core wire 130 resident within hollow guidewire 120, while extended portions near distal end 124 and proximal end 126 of hollow guidewire 120 are uncoated. For example, a coating material such as polytetrafluoroethylene (PTFE) may be dipped or sprayed onto portions of core wire 130 to minimize friction between outer surface 132 of core wire 130 and inner surface 122 of hollow guidewire 120.

Tapered undulating section 140 of core wire 130 provides frictional control of embolic containment device 150 based on a direction of core wire translation within hollow guidewire 120. Tapered undulating section 140 frictionally contacts inner surface 122 of hollow guidewire 120. As core wire 130 is moved distally or proximally relative to hollow guidewire 120, embolic containment device 150 expands or contracts accordingly. Tapered undulating section 140 provides a ratcheting action that allows easier movement in one direction than in another. The relative ease of movement in each direction is controlled, in part, by the number of undulations 142, amplitude 144 of undulations 142, and the degree and direction of the amplitude taper.

Tapered undulating section 140 includes a plurality of undulations 142 along an axial portion of core wire 130 that frictionally contacts inner surface 122 of hollow guidewire 120. Amplitude 144 of each consecutive undulation 142 varies with axial distance from proximal end 136 of core wire 130. For example, the amplitude 144 of each consecutive undulation 142 may increase linearly with distance from proximal end 136 of core wire 130. Alternatively, the amplitude 144 of each consecutive undulation 142 may decrease linearly with distance from proximal end 136 of core wire 130 to provide the desired frictional force in each direction of travel.

In one example, tapered undulating section 140 provides greater friction when core wire 130 axially translates between a proximal position and a distal position than when the core wire axially translates between the distal position and the proximal position. In another configuration, tapered undulating section 140 provides lesser friction when core wire 130 axially translates between a proximal position and a distal position than when core wire 130 axially translates between the distal position and proximal position, based in part on the direction and magnitude of the taper of tapered undulating section 140.

The tapered undulating section 140 of core wire 130 comprises, for example, a crimped set of bends 146 formed in core wire 130 at the time of manufacturing. The set of bends 146 may be formed by a crimping tool or die that bends and deforms core wire 130 at the desired locations along the wire. For example, a die set to form uniform amplitude crimps may be shimmed at one end or the other to achieve the desired degree and direction of taper for the crimps. Crimped undulations 144 have an amplitude, for example, between 0.1 inches and 0.2 inches prior to insertion into hollow guidewire 120, with a spacing between adjacent, opposing peaks on the order of 0.3 inches.

When deployed in the body, embolic containment device 150 is enlarged or expanded to fill a region of the vessel and to temporarily block flow through the vessel, or to filter the fluid flow as it passes through embolic containment device 150. In one embodiment, embolic containment device 150 comprises embolic filter 152. A proximal end of embolic filter 152 is axially fixed to the shaft of hollow guidewire 120, and a distal end of embolic filter 152 is axially fixed to slidable core wire 130 near distal end 134. Embolic filter 152 may be expanded or contracted by pushing or pulling core wire 130 relative to hollow guidewire 120, thereby controlling the relative axial position of the filter ends. Core wire 130 may be held in a fixed open or closed position by friction generated between inner surface 122 of hollow guidewire 120 and a number of specially formed waves or undulations 144 in core wire 130. A portion of core wire 130 is modified to form undulations 144 that create greater holding friction in one direction, as compared to the other direction. For example, pulling core wire 130 requires little resistance to expand embolic filter 152, whereas pushing core wire 130 to contract embolic filter 152 requires significantly more force. Embolic filter 152 is therefore deployed with little force from one direction, and is temporarily held or locked in the expanded configuration by the greater friction in the reverse direction.

In one example, embolic filter 152 includes braided wire mesh 154 that serves as a strainer for fluids that pass through the filter. In another example, embolic filter 152 includes braided wire mesh 154 having at least a portion coated with an elastomeric material 156. The coated portion of braided wire mesh 154 collects and traps emboli while uncoated portions of braided wire mesh 154 allow continued flow of fluid through the vessel. The uncoated portions may comprise, for example, a set of holes, an annular opening, or other suitable opening in the proximal end of embolic filter 152 that cooperates with coated portions to entrain and entrap emboli.

After positioning embolic filter 152 at the desired location in the body, embolic filter 152 is actuated to an expanded configuration when core wire 130 is translated proximally relative to hollow guidewire 120. After treatments are completed, embolic filter 152 is actuated to a contracted configuration as core wire 130 is translated distally relative to hollow guidewire 120, and then the entire system is withdrawn from the body.

Another type of embolic filter 152 expands when core wire 130 is pushed relative to hollow guidewire 120. Frictional forces may be tailored for this and other types of embolic filters 152 by reversing the direction of the taper on undulations 144.

Figure 2A:
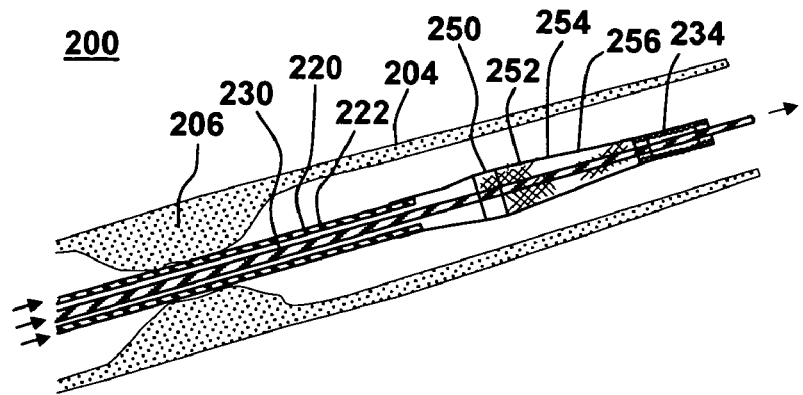
FIG. 2A is a longitudinal cross-sectional view of a portion of a guidewire-based embolic filter system in a contracted state within a vessel, in accordance with one embodiment of the current invention.

FIG. 2A is a longitudinal cross-sectional view of a portion of a guidewire-based embolic filter system in a contracted state within a vessel, in accordance with one embodiment of the present invention at 200. Guidewire-based embolic filter system 200 includes hollow guidewire 220, core wire 230 inserted through hollow guidewire 220, and embolic filter 252, the latter performing as embolic containment device 250. Embolic filter 252 may include a braided mesh 254 to capture embolic material 208. Portions of embolic filter 252 may be coated with elastomeric material 256 to aid in embolic particle collection.

Guidewire-based embolic filter system 200 is moved distal to stenosis 206 being treated and positioned within vessel 204. In this view, embolic filter 252 contracts about core wire 230 and is located distal to stenosis 206. Core wire 230 provides frictional control for the expansion and contraction of embolic filter 252 based on a translational direction of core wire 230 within hollow guidewire 220. A tapered undulating section (not shown) near the proximal end of hollow guidewire 220 provides a predetermined level of friction against inner surface 222 of hollow guidewire 220 to control axial translational motion. The friction aids in retaining embolic filter 252 in the contracted configuration while distal end 234 of core wire 230 is advanced through the vascular system.

Figure 2B:
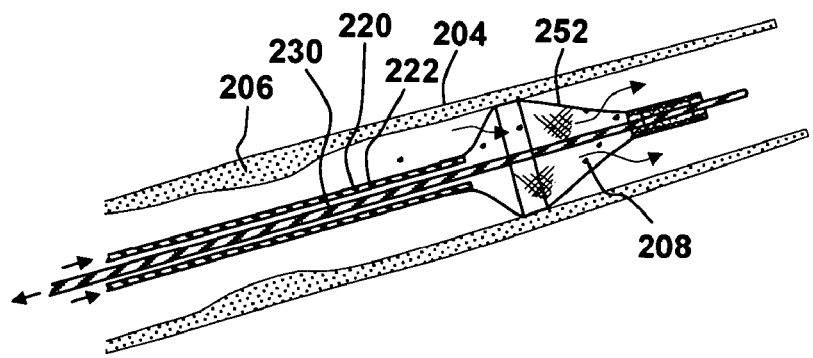
FIG. 2B is a longitudinal cross-sectional view of a portion of a guidewire-based embolic filter system in an expanded state within a vessel, in accordance with one embodiment of the current invention.

FIG. 2B is a longitudinal cross-sectional view of a portion of a guidewire-based embolic filter system in an expanded state within a vessel, in accordance with one embodiment of the present invention. In this view, core wire 230 is positioned at a proximal location with respect to hollow guidewire 220, such that embolic filter 252 is expanded about core wire 230 after embolic filter 252 has been positioned in vessel 204 distal to stenosis 206. In the expanded configuration shown, the tapered undulating section near the proximal end of hollow guidewire 220 provides a predetermined level of friction against inner surface 222 of hollow guidewire 220. The frictional forces help keep embolic filter 252 expanded while hollow guidewire 220 and core wire 230 are positioned. Embolic filter 252 collects embolic material 208 prior to, during and after other treatments to reduce the size or effect of stenosis 206.

Figure 2C:
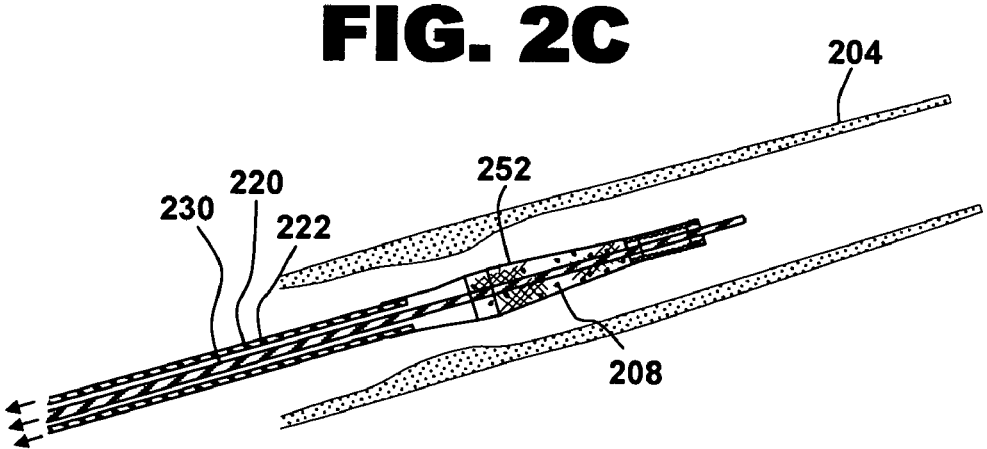
FIG. 2C is a longitudinal cross-sectional view of a portion of a guidewire-based embolic filter system being withdrawn from a vessel, in accordance with one embodiment of the current invention.

FIG. 2C is a longitudinal cross-sectional view of a portion of a guidewire-based embolic filter system being withdrawn from a vessel, in accordance with one embodiment of the present invention. In this view, core wire 230 has been axially translated and is positioned at a distal location with respect to hollow guidewire 220, such that embolic filter 252 is contracted about core wire 230 after embolic filter 252 has collected embolic material 208. The tapered undulating section near the proximal end of hollow guidewire 220 provides a predetermined level of friction against inner surface 222 of hollow guidewire 220. The friction retains embolic filter 252 in the contracted configuration while hollow guidewire 220 and core wire 230 are withdrawn from vessel 204. Embolic material 208 collected by embolic filter 252 is extracted from the body along with hollow guidewire 220 and core wire 230.

Figure 3:
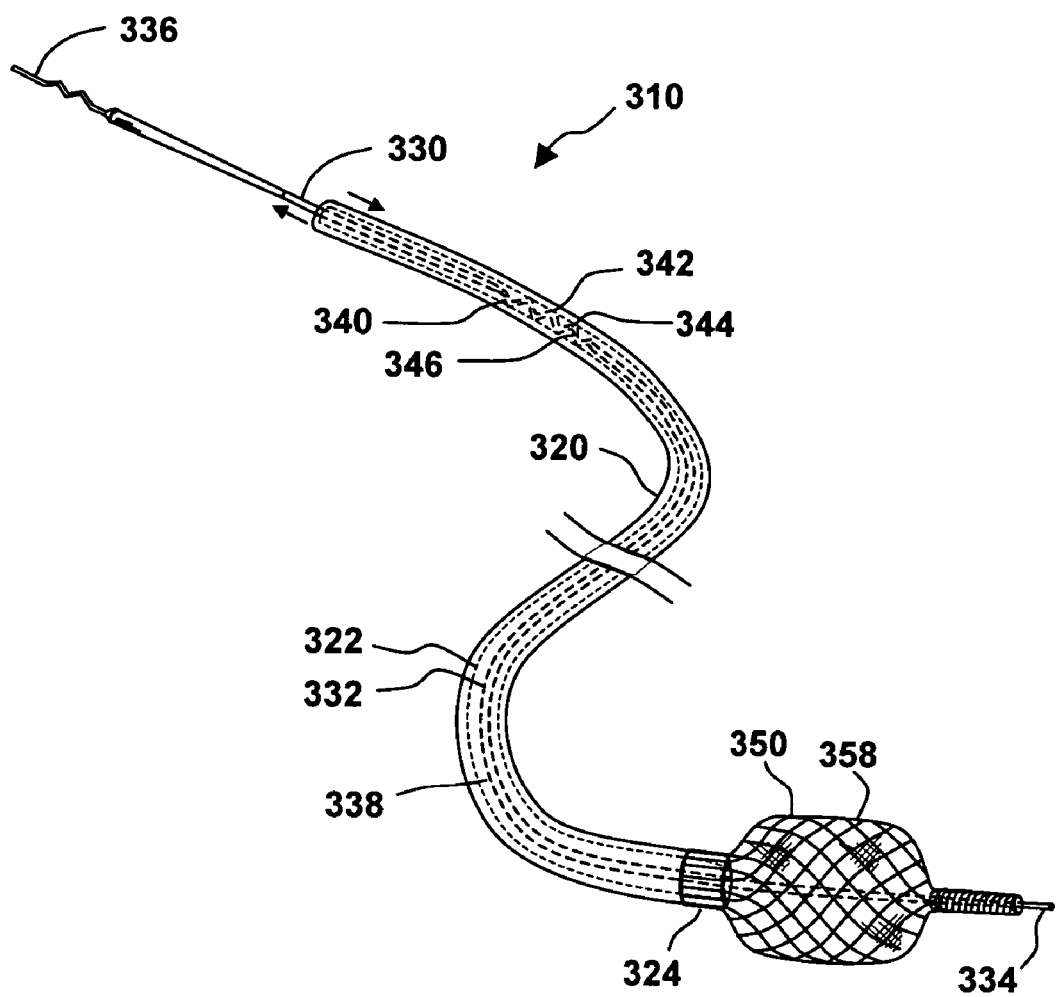
FIG. 3 illustrates a system for treating a vascular condition, in accordance with another embodiment of the current invention.

FIG. 3 illustrates a system for treating a vascular condition, in accordance with another embodiment of the present invention at 300. Embolic containment catheter 310 of vascular condition treatment system 300 includes hollow guidewire 320, core wire 330 having tapered undulating section 340 carried within hollow guidewire 320, and occluder 358 acting as embolic containment device 350. Occluder 358 is coupled between distal end 324 of hollow guidewire 320 and distal end 334 of core wire 330. Tapered undulating section 340 provides tailored friction between core wire 330 and hollow guidewire 320 to control the expansion, contraction, and retention of occluder 358 when in an expanded or a contracted state.

Coating 338 may be disposed on at least a portion of core wire 330 to minimize friction between outer surface 332 of core wire 330 and inner surface 322 of hollow guidewire 320.

Occluder 358 is positioned by inserting core wire 330 and hollow guidewire 320 through an incision, and advancing distal tip or distal end 334 of core wire 330 through blood vessels until the treatment site is reached. When expanded, occluder 358 contains embolic material within a confined, stagnant portion of a vessel. The embolic material is removed, for example, with an aspiration catheter inserted over hollow guidewire 320 after treatments of the vessel are completed.

In the case of a stenosis or a partially occluded vessel, core wire 330 advances occluder 358 distal the treatment site. Once positioned, occluder 358 may be expanded by movement of core wire 330 relative to hollow guidewire 320. An opposite motion closes, compresses, collapses or otherwise contracts occluder 358 prior to extraction from the body.

Tapered undulating section 340 of core wire 330 provides frictional control of occluder 358 based on a direction of core wire translation within hollow guidewire 320. Tapered undulating section 340 frictionally contacts inner surface 322 of hollow guidewire 320. As core wire 330 is moved distally or proximally relative to hollow guidewire 320, occluder 358 expands or contracts accordingly. Tapered undulating section 340 provides a ratcheting action that allows easier movement in one direction than the other. The relative ease of movement in each direction is controlled, in part, by the number of undulations 342, amplitude 344 of each undulation 342, and the degree and direction of taper of amplitudes 344.

Tapered undulating section 340 includes a plurality of undulations 342 along an axial portion of core wire 330. Amplitude 344 of each consecutive undulation 342 varies with axial distance from proximal end 336 of core wire 330. For example, amplitude 344 of each consecutive undulation 342 increases linearly with distance from proximal end 336 of core wire 330. Alternatively, amplitude 344 of each consecutive undulation 342 decreases linearly with distance from proximal end 336 of core wire 330 to provide the desired frictional force in each direction of travel.

In one example, tapered undulating section 340 provides greater friction when core wire 330 axially translates between a proximal position and a distal position than when the core wire axially translates between distal position and proximal position. In another example, tapered undulating section 340 provides less friction when core wire 330 axially translates between the proximal position and the distal position than when core wire 330 axially translates between the distal position and the proximal position. The amount and difference of friction in each axial direction controls the response of occluder 358 to axial translations of core wire 330 relative to hollow guidewire 320.

The tapered undulating section 340 of core wire 330 comprises, for example, a crimped set of bends 346 formed in core wire 330 during manufacture. The set of bends 346 may be formed by a crimping tool that bends and deforms core wire 330 at the desired locations along the wire.

After positioning occluder 358 at the desired location in the body, occluder 358 expands when core wire 330 is translated proximally relative to hollow guidewire 320. When treatments have been completed, occluder 358 is contracted when core wire 330 is translated distally relative to hollow guidewire 320, and the entire system is withdrawn from the body.

In this embodiment, occluder 358 comprises, for example, a self-expanding loosely braided wire structure covered with an attached fabric that enlarges when deployed to fill and temporally occlude the vessel. Occluder 358 blocks fluid flow through a body vessel when occluder 358 is expanded. Occluder 358 is actuated, for example, by an axial translation of core wire 330 within hollow guidewire 320. Tapered undulating section 340 controls, in part, the frictional force between core wire 330 and hollow guidewire 320 as occluder 358 is expanded or contracted. Tapered undulating section 340 also retains occluder 358 in the desired position while other treatments are applied or while hollow guidewire 320 with contracted occluder 358 is positioned or removed from the body.

Figure 4A:
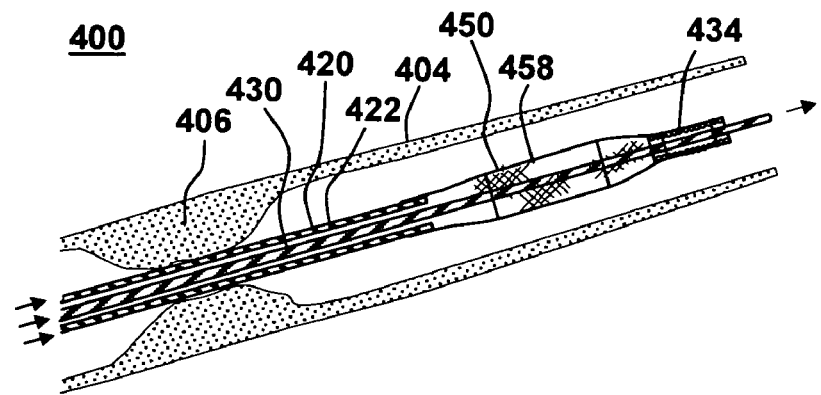
FIG. 4A is a longitudinal cross-sectional view of a portion of a guidewire-based occluder system in a contracted state within a vessel, in accordance with one embodiment of the current invention.

FIG. 4A is a longitudinal cross-sectional view of a portion of a guidewire-based occluder system in a contracted state within a vessel, in accordance with one embodiment of the present invention at 400. Guidewire-based occluder system 400 includes hollow guidewire 420, core wire 430 inserted through hollow guidewire 420, and occluder 458, the latter serving as embolic containment device 450. Occluder 458 includes, for example, a self-expanding loosely braided wire structure covered with an attached fabric that enlarges when deployed to temporally occlude the vessel and contain dislodged embolic material.

Guidewire-based occluder system 400 is moved distal to stenosis 406 being treated and positioned within vessel 404. In this view, occluder 458 contracts about core wire 430 and is located distal to hollow guidewire 420. Core wire 430 provides frictional control for the expansion and contraction of occluder 458 based on a translational direction of core wire 430 within hollow guidewire 420. A tapered undulating section (not shown) near the proximal end of hollow guidewire 420 provides a predetermined level of friction against inner surface 422 of hollow guidewire 420 to control axial translational motion. The friction aids in retaining occluder 458 in the contracted configuration while distal end 434 of core wire 430 is advanced through the vascular system.

Figure 4B:
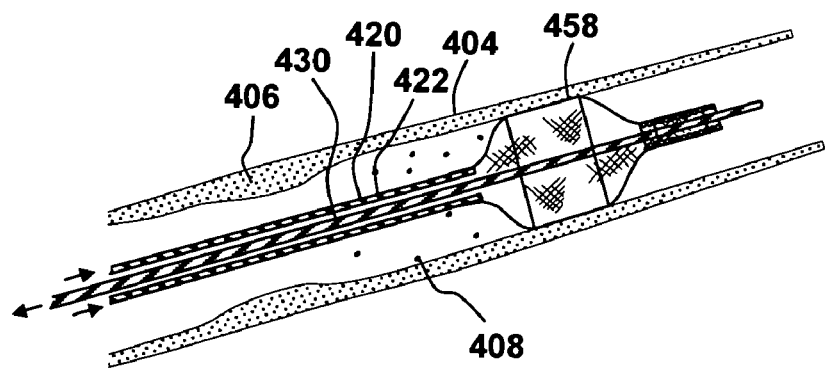
FIG. 4B is a longitudinal cross-sectional view of a portion of a guidewire-based occluder system in an expanded state within a vessel, in accordance with one embodiment of the current invention.

FIG. 4B is a longitudinal cross-sectional view of a portion of a guidewire-based occluder system deployed within a vessel, in accordance with one embodiment of the present invention. In this view, core wire 430 is positioned proximal hollow guidewire 420, such that occluder 458 is expanded about core wire 430 after occluder 458 is positioned in vessel 404 with stenosis 406. The tapered undulating section near the proximal end of hollow guidewire 420 provides a predetermined level of friction against inner surface 422 of hollow guidewire 420. The friction helps retain occluder 458 in the expanded configuration while hollow guidewire 420 and core wire 430 are positioned in the desired location. Occluder 458 contains embolic material 408 within vessel 404 prior to, during and after other treatments to reduce the size or effect of stenosis 406.

Figure 4C:
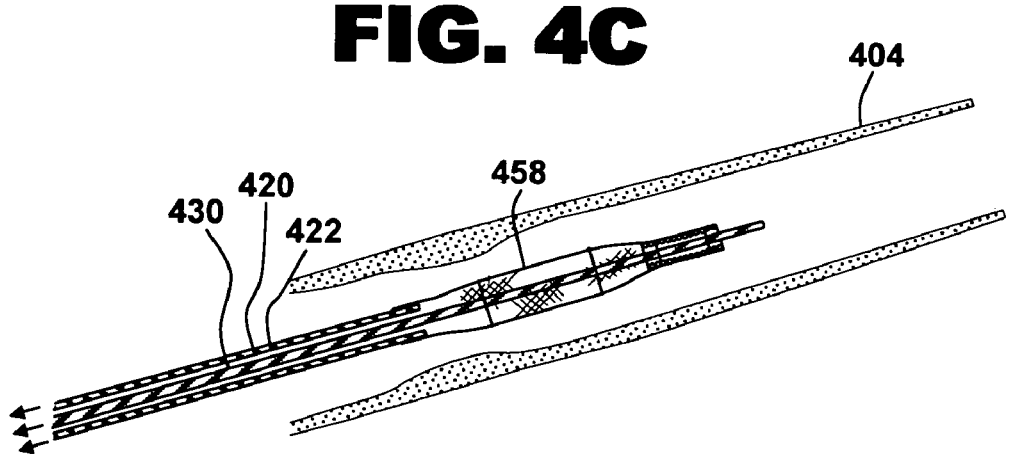
FIG. 4C is a longitudinal cross-sectional view of a portion of a guidewire-based occluder system being withdrawn from a vessel, in accordance with one embodiment of the current invention.

FIG. 4C is a longitudinal cross-sectional view of a portion of a guidewire-based occluder system being withdrawn from a vessel, in accordance with one embodiment of the present invention. In this view, core wire 430 has been axially translated and is positioned at a distal location relative to hollow guidewire 420, such that occluder 458 is contracted about core wire 430 after the embolic material contained by occluder 458 has been aspirated or otherwise removed. The tapered undulating section near the proximal end of hollow guidewire 420 provides a predetermined level of friction against inner surface 422 of hollow guidewire 420 to help keep occluder 458 contracted while hollow guidewire 420 and core wire 430 are withdrawn from vessel 404.

Figure 5:
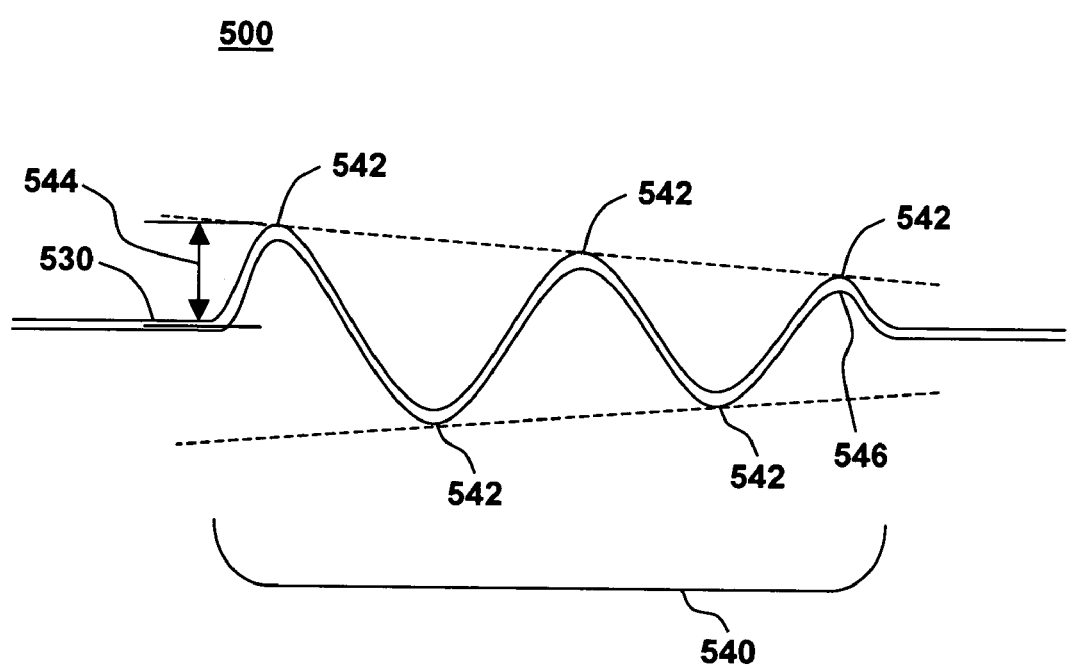
FIG. 5 illustrates a tapered undulating section of a core wire, in accordance with one embodiment of the current invention.

FIG. 5 illustrates a tapered undulating section of a core wire, in accordance with one embodiment of the present invention at 500. Tapered undulating section 540 includes a plurality of undulations 542 along an axial portion of core wire 530. Amplitude 544 of each consecutive undulation 542 decreases with distance from the proximal end of core wire 530 to provide the desired frictional force in each direction of travel. Tapered undulating section 540 of core wire 530 comprises, for example, a crimped set of bends 546 formed in core wire 530 during manufacture. The set of bends 546 may be formed in a crimping tool that bends and deforms core wire 530 at the desired locations along the wire. When the crimps are tapered, the force required to move against the taper increases and the force required to move in the direction of the taper decreases.

In this example, tapered undulating section 540 provides less friction with the hollow guidewire when core wire 530 axially translates between a proximal position and a distal position than when the core wire axially translates between the distal position and the proximal position. That is, less friction occurs when core wire 530 is pushed from left to right, as shown in FIG. 5, than when core wire 530 is pushed from right to left. This feature may be used to preferentially keep the filter or occluder from prematurely opening or closing, depending on which direction the tapered crimps are set on the core wire.

Figure 6:
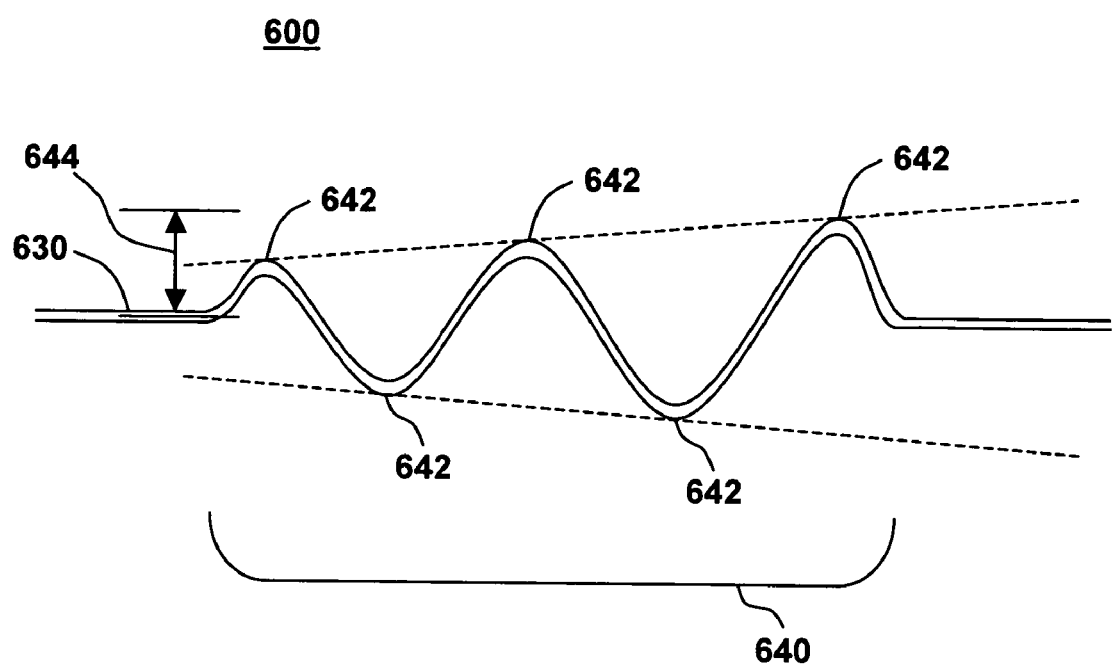
FIG. 6 illustrates a tapered undulating section of a core wire, in accordance with another embodiment of the current invention.

FIG. 6 illustrates a tapered undulating section of a core wire, in accordance with another embodiment of the present invention at 600. Tapered undulating section 640 includes a plurality of undulations 642 along an axial portion of core wire 630. Amplitude 644 of each consecutive undulation 642 increases with distance from the proximal end of core wire 630 to provide the desired frictional force in each direction of travel.

In this example, tapered undulating section 640 provides greater friction when core wire 630 axially translates between a proximal position and a distal position than when the core wire axially translates between the distal position and the proximal position.

Figure 7:
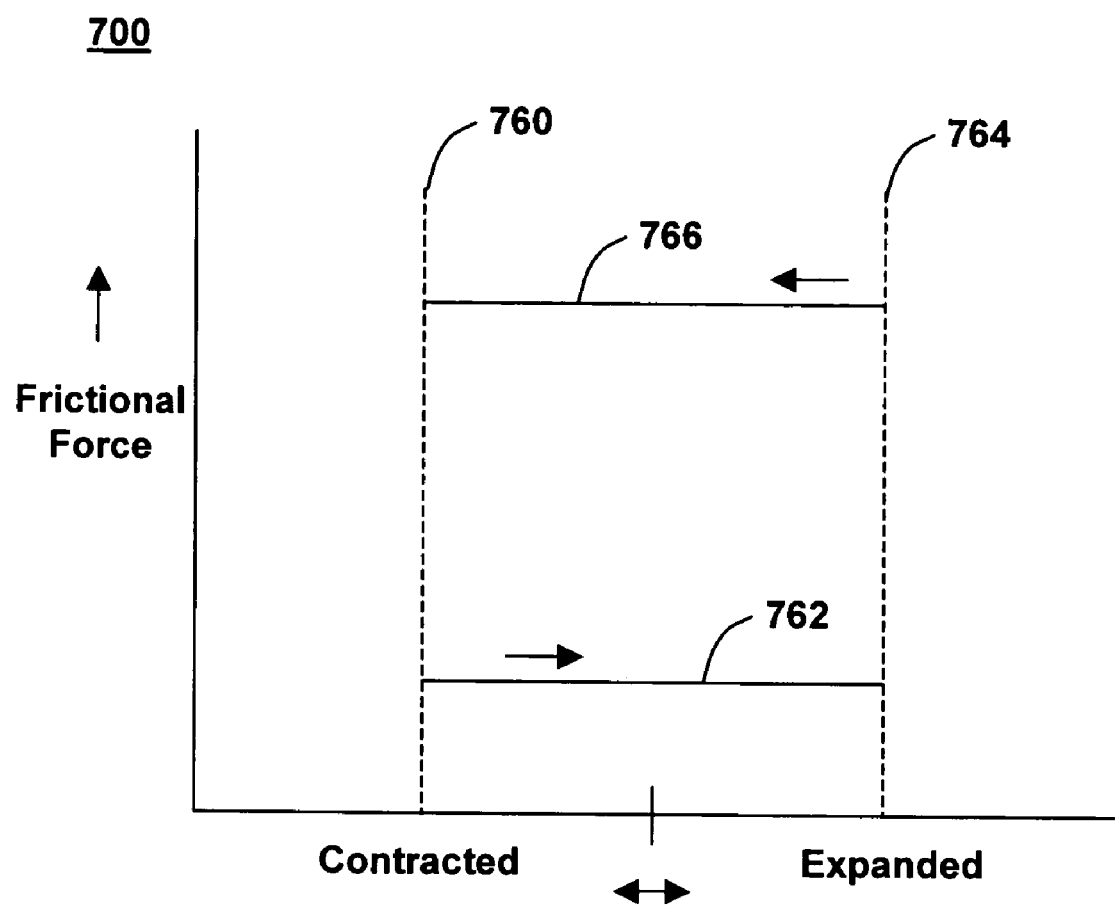
FIG. 7 is a plot of frictional force versus the direction of axial translation of a core wire with a tapered undulating section, in accordance with one embodiment of the current invention.

FIG. 7 is a plot of frictional force versus the direction of core wire translation, in accordance with one embodiment of the present invention at 700. When the core wire is in a distal position relative to the hollow guidewire, the emboli containment device is in a compressed or contracted configuration 760. To expand or enlarge the emboli containment device, the core wire is axially translated within the hollow guidewire from contracted configuration 760 along line 762 to an expanded configuration 764. The tapered undulating section of the core wire is configured with relatively low frictional force as the core wire makes the axial transition in the first direction.

When the core wire is in a proximal position relative to the hollow guidewire, the emboli containment device is in the expanded configuration 764. To collapse or contract the emboli containment device, the core wire is axially translated in an opposite direction within the hollow guidewire from the expanded configuration 764 along line 766 back to contracted configuration 760. The tapered undulating section of the core wire is configured with relatively high frictional force as the core wire makes the axial transition in the second direction, such that the emboli containment device is maintained, for example, in the expanded configuration without inadvertent contraction while performing treatments.

In some cases, the wire framework of the embolic containment device is pre-shaped to be in either a normally expanded state or a normally contracted state when unconstrained. The frictional characteristics of the core wire can be adjusted to balance or augment the additional force required to contract or expand the embolic containment device, accordingly. In one example, the degree and direction of taper of the core wire undulations counter the additional force, so that the user or practitioner feels an approximately equal force whether expanding or contracting the embolic containment device. In another example, the degree and direction of taper of the core wire undulations augment the frictional force shown in FIG. 7, so that the expanded embolic containment device remains locked and is less apt to contract when expanded, and is easier to expand when contracted.

FIG. 8 shows a flow diagram of a method of treating a vascular condition, in accordance with one embodiment of the present invention at 800. Vascular condition treatment method 800 may involve catheter-based tools that generate emboli and other particulate material, which need to be caught or contained and withdrawn, aspirated, or otherwise removed from the vessel. The treatments may include angioplasty, atherectomy, stent deployment and other intravascular procedures.

Vascular condition treatment method 800 includes steps to expand and contract an embolic containment device coupled to the distal ends of a hollow guidewire and a core wire inserted through the hollow guidewire. One or more vascular treatments may be applied for the prevention or correction of various ailments and deficiencies, including those associated with the cardiovascular system, the cerebrovascular system, urogenital systems, biliary conduits, abdominal passageways and other biological vessels within the body.

An embolic containment catheter including a core wire inserted through a hollow guidewire and an embolic containment device is provided, as seen at block 805. The core wire has a tapered undulating section carried within the hollow guidewire that provides frictional control of the embolic containment device based on a direction of core wire translation within the hollow guidewire. The tapered undulating section frictionally contacts an inner surface of the hollow guidewire. Based on the desired intent, the tapered undulating section may provide greater friction when the core wire axially translates between a proximal position and a distal position. In other configurations, the tapered undulating section may provide less friction when the core wire axially translates between the proximal position and the distal position. The tapered undulating section of the core wire may comprise, for example, a crimped set of bends formed in the core wire.

The tapered undulating section includes, for example, a plurality of undulations along an axial portion of the core wire. The amplitude of each consecutive undulation varies with axial distance from a proximal end of the core wire. The amplitude of two or more consecutive undulations may increase linearly, for example, with distance from the proximal end of the core wire. Alternatively, the amplitude of two or more consecutive undulations may decrease linearly with distance from the proximal end of the core wire. One or more undulations in the section may have equal amplitudes.

The embolic containment device such as an embolic filter or an occluder is coupled between a distal end of the hollow guidewire and a distal end of the core wire. The embolic filter includes, for example, a braided wire mesh having portions coated with an elastomeric material to contain pieces of embolic material. The occluder has, for example, a loosely braided wire with an elastic membrane attached to the wire to block the flow of fluid through the vessel.

The embolic containment catheter with the hollow guidewire, core wire, and the embolic containment device is inserted and positioned in a vessel of the body. The hollow guidewire with the embolic containment device at the distal end is manipulated manually through the vascular system to the desired location for placement of the device. For example, a needle puncture is made in the body near the femoral artery, and the hollow guidewire with the embolic containment device is inserted through the puncture, through the femoral artery, and into a position within a blood vessel where the embolic containment device is to be expanded. Prior to the positioning of the embolic containment catheter, fluoroscopic contrast fluid may be injected into the blood vessel in order to identify, visualize and verify the location of a stenosis, blockage, or other medical condition within the blood vessel.

The core wire is axially translated in a first direction relative to the hollow guidewire, as seen at block 810. The embolic containment device is actuated and expanded when the core wire is axially translated in the first direction. To axially translate the core wire relative to the hollow guidewire, a core wire handle may be attached to the proximal end of the core wire extending from the hollow guidewire, which allows the medical practitioner to readily grasp the handle and control the movement of the core wire within the hollow guidewire. A liner may be included between the core wire and the hollow guidewire to retain and center the core wire within the hollow guidewire when the hollow guidewire and core wire curve and bend within the sinuous vasculature.

The axial translation in the first direction is controlled based on frictional resistance between the tapered undulating section and an internal surface of the hollow guidewire. For example, the embolic filter is actuated to an expanded configuration when the core wire is translated proximally relative to the hollow guidewire or when the hollow guidewire is translated distally relative to the core wire. The core wire handle, when used, may then be removed to allow treatment catheters to be positioned over the hollow guidewire.

With the embolic containment device in an expanded configuration, various medical treatments and procedures may be performed, as seen at block 815. The medical procedures include, for example, delivering an angioplasty balloon catheter over the hollow guidewire to inflate a balloon at the treatable region, or inserting a stent-delivery catheter to deploy a stent at the desired place in the vessel. Other treatments include advancing drug-delivery catheters or inspection catheters over the hollow guidewire to the point of treatment. Other procedures may use a dilation catheter, a stent-delivery catheter, an aspiration catheter, a measurement catheter, an angioplasty catheter, an atherectomy catheter, an ultrasound device, a measurement device, a laser catheter, an imaging catheter, a treatment catheter, a therapy catheter, or combinations thereof.

During treatments, embolic material may be captured or contained by the expanded embolic containment device. When an embolic filter is used, the embolic material is captured while blood continues to flow through the vessel. When an occluder is used, the vessel is blocked temporarily to contain the embolic particles, which may be removed, for example, with an aspiration catheter prior to removal of the occluder. The aspiration catheter is inserted over the hollow guidewire to remove the entrapped emboli. When the treatments have been completed, the treatment catheters are removed and the core wire handle may be reattached if desired.

The core wire is axially translated in a second direction relative to the hollow guidewire, as seen at block 820. The embolic containment device is closed, compressed, collapsed or otherwise contracted within the vessel based on the axial translation in the second direction. In one example, the embolic containment device is actuated to a contracted configuration when the core wire is axially translated in the second direction. The embolic containment device is contracted as the core wire is translated to a distal position within the hollow guidewire. In another example, the embolic containment device is actuated to a contracted configuration when the core wire is translated distally relative to the hollow guidewire.

The axial translation in the second direction is controlled based on frictional resistance between the tapered undulating section and the internal surface of the hollow guidewire. In one example, the required amount of frictional resistance for the expanded configuration of the embolic containment device is set higher than the required amount frictional resistance for the contracted configuration.

When the treatments are completed, the hollow guidewire, core wire, and embolic containment device are removed from the vessel and repositioned or otherwise discarded, as seen at block 825.

Variations and alterations in the design, manufacture and use of the guidewire-based embolic filter, occluder or other containment device are apparent to one skilled in the art, and may be made without departing from the spirit and scope of the present invention. Additionally, the invention may be applied to a variety of push-pull wire-like devices, such as a low-profile valve for an occlusion balloon catheter or catheters with mechanisms that anchor temporarily onto the vessel walls. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vascular condition, the system comprising:
    a hollow guidewire;
    a core wire inserted through the hollow guidewire, the core wire including a tapered undulating section including a plurality of undulations along an axial portion of the core wire, wherein an amplitude of each consecutive undulation varies with axial distance from a proximal end of the core wire, the plurality of undulations frictionally contacting an inner surface of the hollow guidewire when disposed therein; and
    an embolic containment device coupled between a distal end of the hollow guidewire and a distal end of the core wire.

2. The system of claim 1 wherein the amplitude of each consecutive undulation increases linearly with distance from the proximal end of the core wire.

3. The system of claim 1 wherein the amplitude of each consecutive undulation decreases linearly with distance from the proximal end of the core wire.

4. The system of claim 1 wherein the tapered undulating section provides greater friction when the core wire axially translates between a proximal position and a distal position than when the core wire axially translates between the distal position and the proximal position.

5. The system of claim 1 wherein the tapered undulating section provides lesser friction when the core wire axially translates between a proximal position and a distal position than when the core wire axially translates between the distal position and the proximal position.

6. The system of claim 1 wherein the tapered undulating section of the core wire comprises a crimped set of bends formed in the core wire.

7. The system of claim 1 wherein the embolic containment device comprises an embolic filter.

8. The system of claim 7 wherein the embolic filter includes a braided wire mesh, and wherein at least a portion of the braided wire mesh is coated with an elastomeric material.

9. The system of claim 1 wherein the embolic containment device is actuated to an expanded configuration when the core wire is translated proximally relative to the hollow guidewire.

10. The system of claim 1 wherein the embolic containment device is actuated to a contracted configuration when the core wire is translated distally relative to the hollow guidewire.

11. The system of claim 1 wherein the embolic containment device comprises an occluder.

12. The system of claim 11 wherein the occluder blocks fluid flow through a body vessel when the occluder is actuated, the occluder being actuated by an axial translation of the core wire within the hollow guidewire.

13. The system of claim 1 further comprising;
a coating disposed on at least a portion of the core wire, wherein the coating reduces friction between the coated portions of the core wire and an inner surface of the hollow guidewire.

14. A method of treating a vascular condition, the method comprising:
providing a core wire inserted through a hollow guidewire, the core wire including a tapered undulating section including a plurality of undulations along an axial portion of the core wire, wherein an amplitude of each consecutive undulation varies with axial distance from a proximal end of the core wire, the plurality of undulations frictionally contacting an inner surface of the hollow guidewire when disposed therein;
providing an embolic containment device coupled between a distal end of the hollow guidewire and a distal end of the core wire;
axially translating the core wire in a first direction relative to the hollow guidewire to expand the embolic containment device; and
axially translating the core wire in a second direction relative to the hollow guidewire to contract the embolic containment device.

15. The method of claim 14 further comprising:
capturing embolic material when the embolic containment device is expanded.

16. The method of claim 14, wherein the embolic containment device includes one of an embolic filter and an occluder.

17. A guidewire-based embolic containment system comprising:
a hollow guidewire;
a core wire slidably inserted through the hollow guidewire, the core wire including frictional control means disposed within the hollow guidewire such that axial movement of the core wire within the hollow guidewire is easier in a first direction than in a second, opposite direction; and
an embolic containment device coupled between a distal end of the hollow guidewire and a distal end of the core wire.

18. The guidewire-based embolic containment system of claim 17 wherein the axial movement of the core wire within the hollow guidewire is easier in a distal direction than in a proximal direction.

19. The guidewire-based embolic containment system of claim 17 wherein the embolic containment device comprises an embolic filter.

* * * * *